US007011847B2

(12) United States Patent
Lulla et al.

(10) Patent No.: US 7,011,847 B2
(45) Date of Patent: Mar. 14, 2006

(54) ENTERIC COATED FORMULATION FOR BISPHOSPHONIC ACIDS AND SALTS THEREOF

(75) Inventors: Amar Lulla, Colabam Mumbai (IN); Geena Malhotra, Mumbai (IN)

(73) Assignee: U & I Pharmaceuticals Ltd., Long Island, NY (US)

(*) Notice: Subject to any disclaimer, the term of this patent is extended or adjusted under 35 U.S.C. 154(b) by 126 days.

(21) Appl. No.: 10/686,528

(22) Filed: Oct. 16, 2003

(65) Prior Publication Data

US 2004/0161460 A1 Aug. 19, 2004

Related U.S. Application Data

(63) Continuation of application No. 09/669,635, filed on Sep. 26, 2000, now Pat. No. 6,676,965.

(30) Foreign Application Priority Data

| Oct. 20, 1999 | (IN) | ................... 23/BOM-WTO/99 |
| Oct. 20, 1999 | (IN) | .......................... 709/BOM/99 |
| Oct. 20, 1999 | (IN) | .......................... 710/BOM/99 |

(51) Int. Cl.
*A61K 9/23* (2006.01)

(52) U.S. Cl. ...................... 424/458; 424/461; 424/462; 424/463; 424/464; 424/465; 424/474; 424/480

(58) Field of Classification Search ............... 424/474, 424/475, 480, 482, 494, 497
See application file for complete search history.

(56) References Cited

U.S. PATENT DOCUMENTS

| 3,962,432 | A | 6/1976 | Schmidt-Dünker |
| 4,054,598 | A | 10/1977 | Blum et al. |
| 4,122,157 | A | 10/1978 | Huber |
| 4,248,858 | A | 2/1981 | Guley et al. |
| 4,267,108 | A | 5/1981 | Blum et al. |
| 4,309,404 | A | 1/1982 | DeNeale et al. |
| 4,309,405 | A | 1/1982 | Guley et al. |
| 4,309,406 | A | 1/1982 | Guley et al. |
| 4,327,039 | A | 4/1982 | Blum et al. |
| 4,407,761 | A | 10/1983 | Blum et al. |
| 4,621,077 | A | 11/1986 | Rosini et al. |
| 4,624,947 | A | 11/1986 | Blum et al. |
| 4,746,654 | A | 5/1988 | Breliere et al. |
| 4,794,001 | A | 12/1988 | Mehta et al. |
| 4,922,007 | A | 5/1990 | Kieczykowski et al. |
| 4,927,814 | A | 5/1990 | Gall et al. |
| 5,096,717 | A | 3/1992 | Wirth et al. |
| 5,358,941 | A | 10/1994 | Bechard et al. |
| 5,431,920 | A * | 7/1995 | Bechard ..................... 424/480 |
| 5,681,590 | A | 10/1997 | Bechard et al. |
| 5,776,499 | A | 7/1998 | Pohjala et al. |
| 5,849,726 | A | 12/1998 | Brenner et al. |
| 5,935,602 | A | 8/1999 | Dansereau et al. |
| 6,391,342 | B1 | 5/2002 | Henriksen et al. |
| 6,465,017 | B1 | 10/2002 | Tomer et al. |
| 6,676,965 | B1 * | 1/2004 | Lulla et al. ................. 424/458 |

FOREIGN PATENT DOCUMENTS

| EP | 0252504 | 7/1987 |
| EP | 0421921 | 8/1990 |
| WO | WO 93/09785 | 5/1993 |
| WO | WO 95/08331 | 9/1994 |
| WO | WO 98/52564 | 11/1998 |
| WO | WO 99/09995 | 3/1999 |
| WO | WO 99/48498 | 9/1999 |

* cited by examiner

*Primary Examiner*—Thurman K. Page
*Assistant Examiner*—Pili A. Hawes
(74) *Attorney, Agent, or Firm*—Venable LLP; Julie A. Petruzzelli; Keith G. Haddaway

(57) ABSTRACT

Pharmaceutical compositions and methods of using the composition are provided. The pharmaceutical composition comprises an inert core surrounded by an active coating containing one or more bisphosphonic acids or salts thereof, a seal coating surrounding the active coating and an enteric coating surrounding the seal coating. Alendronic acid and alendronate sodium trihydrate are the preferred active ingredients. The composition may be provided in the form of pellets in a capsule or Peltabs. The invention further provides methods for the treatment of disorders caused by the abnormal dissolution or deposition of calcium salts using the inventive compositions.

22 Claims, No Drawings

ENTERIC COATED FORMULATION FOR BISPHOSPHONIC ACIDS AND SALTS THEREOF

This application is a continuation of U.S. application Ser. No. 09/669,635, filed Sep. 26, 2000 Now U.S. Pat. No. 6,676,955, which claims priority to Indian Application Nos. 710/BOM/99 and 23/BOM-WTO/99 (709/BOM/99), both of which were filed on Oct. 10, 1999, each of which is incorporated herein by reference in its entirety.

BACKGROUND OF THE INVENTION

1. Field of the Invention

The present invention relates to a pharmaceutical composition, a process of preparing the pharmaceutical composition and a method of using the pharmaceutical composition. Specifically, the invention provides a pharmaceutical composition containing bisphosphonic acids or salts thereof for use in the treatment of osteoporosis and other disorders caused by the abnormal dissolution or deposition of calcium salts.

2. Background of the Invention

Methods of preparing bisphosphonic acids are set forth in U.S. Pat. No. 3,962,432; U.S. Pat. No. 4,054,598; U.S. Pat. No. 4,267,108; U.S. Pat. No. 4,327,039; U.S. Pat. No. 4,407,761; U.S. Pat. No. 4,621,077; U.S. Pat. No. 4,624,947; U.S. Pat. No. 4,746,654; U.S. Pat. No. 4,922,007; and EPO Patent Pub. No. 0,252,504. In particular, methods for the preparation of 4-amino-1-hydroxybutylidene- 1,1-bisphosphonic acid and 4-amino-1-hydroxy-butylidene-1,1-bisphosphonic acid monosodium salt trihydrate may be found in U.S. Pat. No. 4,407,761 and U.S. Pat. No. 4,922,007, respectively.

The pharmaceutical compositions containing the bisphosphonic acids and salts set forth in the patents listed above have the disadvantage that the active ingredients are released from the medications almost instantaneously in the upper gastrointestinal tract causing esophageal discomfort and ulceritis. Thus, the medications have to be taken on arising for the day and at least 30 minutes before the first food, beverage or medication with a full glass (200 ml) of plain water only. The patients are advised to sit upright for about 30 minutes after ingestion of the medication and until their first food of the day. Patients are instructed not to take medication at bedtime or before arising for the day. See Physician's Desk Reference (U.S.) Product Information, 1999, p. 1798.

Several problems have been noted in the preparation of tablet formulations comprising bisphosphonic acid active ingredients, and in particular with enteric coated forms of these active ingredients. For example, U.S. Pat. No. 5,431,920 points out that "standard methods for tablet formulation of bisphosphonic acids suffer from serious difficulties." Thus, particular dry mix formulations are required when formulating tablets from these active ingredients. In addition, this same patent points out that "[e]nteric coated dosage forms can suffer from stability problems as a result of interactions between the active drug and the acidic enteric coatings."

The present invention solves these problems by providing dosage forms of bisphosphonic acids that do not require formulation into tablets. The dosage forms of the present invention also have improved stability as compared to prior art formulations.

SUMMARY OF THE INVENTION

In summary, the invention is related to pharmaceutical compositions comprising bisphosphonic acids and salts thereof, their preparation and method of use. More specifically, the invention is related to pharmaceutical compositions comprising alendronic acid and related compounds or salts thereof surrounding an inert core, which is covered with a seal coating which is further covered with an enteric coating.

The invention provides pharmaceutical compositions for the treatment of disorders caused by the abnormal dissolution or deposition of calcium salts. The pharmaceutical compositions of the invention comprise an inert core, an active coating containing at least one bisphosphonic acid or salt thereof surrounding the inert core, a seal coating surrounding the active coating, and an enteric coating around the seal coating. Preferred bisphosphonic acids are selected from the group consisting of 4-amino-1-hydroxybutylidene-1,1-bisphosphonic acid, N-methyl-4-amino-1-hydroxy-butylidene-1,1-bisphosphonic acid, 4-(N,N-dimethylamino)-1-hydroxybutyl-idene-1,1-bisphosphonic acid, 3-amino-1-hydroxypropylidene-1,1-bisphosphonic acid, 3-(N,N-dimethylamino)-1-hydroxy-propylidene-1,1-bisphosphonic acid, 1-hydroxy-3-(N-methyl-N-pentylamino)propylidene-1,1-bisphosphonic acid, and 4-(hydroxymethylene-1,1-bisphosphonic acid)-piperidine. Alendronic acid is a particularly preferred acid and alendronate sodium trihydrate is a particularly preferred salt. Other preferred salts include etidronate, clodronate, pamidronate, and ibandronate. The compositions preferably comprise from about 4% to about 40% by weight of at least one bisphosphonic acid or salt.

Typical enteric coatings for use in the invention include one or more of hydroxypropyl methylcellulose phthalate, hydroxypropyl cellulose acetyl succinate, cellulose acetate phthalate, polyvinyl acetate phthalate, and methacrylic acid-methyl methacrylate copolymers.

The active ingredient is coated onto an inert core, such as nonpareils in the form of sugar beads or sugar/starch beads, to form the active core. The composition may further contain pharmaceutically acceptable excipients, diluents, binders, solubilizers, lubricants, disintegrants, etc. In particular, the active core is formed by applying an active coating to the inert core. The active coating comprises the active ingredient and may further comprise a polymer. Preferred polymers include hydroxypropyl methicellulose, hydroxypropyl cellulose and polyvinyl pyrrolidone Compositions according to the invention may be in the form of enteric coated beads in gelatin capsules or Peltabs, and the invention further provides a process for preparing the claimed compositions in these forms. The gelatin capsules or Peltabs may themselves be coated with an enteric coating. The inventive compositions are preferentially released in the lower gastrointestinal tract upon ingestion and thus avoid the disadvantages described above for the prior art.

The invention also provides methods for the treatment of disorders caused by the abnormal dissolution or deposition of calcium salts by treating a patient in need of such treatment with a therapeutically effective amount of the inventive compositions. Disorders caused by the abnormal dissolution or deposition of calcium salts that may be treated by the compositions of the invention include osteoporosis, osteodystrophy, Paget's disease, myositis ossificans, Bechterew's disease, cholelithiasis, nephrolithiasis, urinary calculus, arteriosclerosis, arthritis, bursitis, neuritis and tetany. The compositions are particularly useful for the treatment of osteoporosis.

The above objectives and advantages of the invention are illustrative, and not exhaustive, of those which can be achieved by the invention. The examples presented herein are non-limiting. Thus, these and other objectives and advantages of the invention will be apparent from the description herein, both as embodied herein and as modified in view of any variations which will be apparent to those skilled in the art.

DETAILED DESCRIPTION OF THE INVENTION

The present invention provides a pharmaceutical composition comprising from about 4% to about 40% by weight of at least one 1,1-bisphosphonic acid or salt thereof as an active ingredient. The 1,1-bisphosphonic acid is preferably selected from the group consisting of:
- 4-amino-1-hydroxybutylidene-1,1-bisphosphonic acid;
- N-methyl-4-amino-1-hydroxybutylidene-1,1-bisphosphonic acid;
- 4-(N,N-dimethylamino)-1-hydroxybutylidene-1,1-bisphosphonic acid;
- 3-amino-1-hydroxypropylidene-1,1-bisphosphonic acid;
- 3-(N,N-dimethylamino)-1-hydroxypropylidene-1,1-bisphosphonic acid;
- 1-hydroxy-3-(N-methyl-N-pentylamino)propylidene-1,1-bisphosphonic acid; and
- 4-(hydroxymethylene-1,1-bisphosphonic acid)-piperidine.

In the present invention, the preferred active ingredient is 4-amino-1-hydroxybutylidene-1,1-bisphosphonic acid, i.e. alendronic acid, and, more preferably, its monosodium salt trihydrate, alendronate sodium trihydrate. Other bisphosphonic acids or salts thereof may be used as well, including, for example, etidronate, clodronate, pamidronate or ibandronate. Suitable salts for use in the present invention may be formed with, for example, alkali metals, amines and alkanol amines. Salts may be formed by reacting the acid with an alkali metal hydroxide (e.g. LiOH, NaOH), alkali metal carbonates (e.g. $Na_2CO_3$), lower alkylamines (e.g. methylamine), lower alkanolamines (e.g. ethanolamine, diethanolamine, triethanolamine) or quaternary ammonium salts (e.g. tetramethylammonium hydroxide).

The invention provides pharmaceutical compositions for oral administration substantially comprising an inert core, an active coating having at least one bisphosphonic acid or salt thereof surrounding the inert core, a seal coating surrounding the active coating and an acid resistant coating (the "enteric coating") surrounding the seal coating. The present invention thus is able to resist the acidic environment of the stomach and avoid the release of the medication in the upper gastrointestinal tract where it may cause esophageal or stomach discomfort or ulceritis. Accordingly, the disadvantages described above for the prior art compositions are overcome by the present invention.

The active core may be achieved by any process known in the art of making pellets, for example, extrusion spheronization, centrifugal coating, wurster coating, and others. According to the invention, an active core may be formed on an inert core, such as non-pareils, by applying an active coating comprising at least one bisphosphonic acid or salt. The bisphosphonic acids or salts may be mixed with pharmaceutically acceptable components, such as binding agents, solubilizers, lubricants, diluents, disintegrants, etc., prior to forming the active coating on the inert core. In addition, the bisphosphonic acid or salt thereof may be applied with a polymer to form a polymer film. Preferred polymers are hydroxypropyl methylcellulose, hydroxypropyl cellulose and polyvinyl pyrrolidone.

The active core containing the bisphosphonic acid or salt may be coated with a hydrophilic polymer known in the art, i.e. a seal coating. A suitable seal coating may comprise, for example, hydroxypropyl methylcellulose (HPMC), hydroxypropyl cellulose (HPC), polyvinyl pyrrolidone (PVP), shellac, cellulose gums and xanthan gums. The seal coated active core is then further coated with an enteric coating.

A wide variety of conventional enteric coatings may be employed in the present invention, including, for example: cellulose acetate phthalate; hydroxypropyl methylcellulose phthalate (HPMCP); hydroxypropyl cellulose acetyl succinate; polyvinyl acetate phthalate; copolymerized methacrylic acid/methacrylic acid methyl esters, such as Eudragit L 12.5, Eudragit L 100 55, and Eudragit S 100; and mixtures thereof. The enteric coating may further contain conventional plasticizers, pigments and/or dispersants, including, for example, polyethylene glycols, triacetin, triethyl citrate, Citroflex and dibutyl sebacate.

The enteric coating may be applied in any suitable manner known in the art, such as, for example, by using a Wurster coater. When applied, the enteric coating may be in the form of an aqueous dispersion in water or other dispersing medium, or in the form of a solution. If the enteric coating is applied in the form of a dispersion or solution, it is preferred that the dispersion or solution be treated with an alkali prior to applying the enteric coating to the active core in order to neutralize at least part of any free acid content. The alkali may be, for example, a carbonate or a hydroxide of sodium, potassium, magnesium or calcium.

Bisphosphonic acids and salts thereof that may be incorporated into the formulations according to the present invention have been found to be useful in treating a variety of disorders in mammals. These disorders generally relate to abnormalities of calcium or phosphate metabolic pathways and particularly to the abnormal dissolution or deposition of calcium salts. Disorders that have been found to be treatable using bisphosphonic acids and salts include osteoporosis, osteodystrophy, Paget's disease, myositis ossificans, Bechterew's disease, cholelithiasis, nephrolithiasis, urinary calculus, arteriosclerosis, arthritis, bursitis, neuritis and tetany. The pharmaceutical compositions prepared according to the invention are particularly useful for the treatment of osteoporosis.

The dosages of the compounds may be variable and depend on the particular condition to be treated and other factors including the severity of the illness, duration of treatment and the identity of the particular compounds being used. Effective dosages preferably range from about 0.05 to about 500 mg/kg body weight/day and more preferably from about 1 to about 50 mg/kg/day. The dosage is typically administered in 4 individual doses. After initial treatment with a relatively high dose, it may be necessary to continue treatment at a lower dose to maintain the beneficial effects of the compounds.

Pharmaceutical compositions according to the present invention may further comprise one or more additives. Examples of particularly useful additives include diluents to aid dissolution of the pharmaceutically active ingredient and lubricants to aid flow of the active ingredient during manufacture. The diluent may be, for example, lactose. The lubricant may be, for example, magnesium stearate and/or talcum. It will be appreciated that the pharmaceutical compositions of the invention may also contain any one or more other additives conventionally used in the formulation of pharmaceutical compositions. Additives may include excipients known in the art of manufacturing capsules and Peltabs, such as lactose, microcrystalline cellulose, dicalcium phosphate, starch, sugar, and disintegrants (e.g., starch and derivatives of starch, sodium carboxy methyl cellulose and its derivatives, and crospovidone).

The pharmaceutical composition of the present invention may take the form of Peltabs or pellets in a capsule. The disadvantages of forming tablets containing bisphosphonic acids described in the prior art are thus avoided. A further advantage of the invention is that the capsule or Peltab can break down in the stomach releasing the enteric coated beads which can then move freely into the lower gastrointestinal tract. This avoids problems associated with a tablet sitting in the stomach until the digestion of food opens the pyloric sphincter and the tablet passes into the duodenum. In addition, the use of small beads decreases the risk of large local concentrations of the active ingredients coming into contact with mucosal or epithelial tissue.

The relative release rate of the active ingredient from the enteric coated beads may be varied by changing one or more of (a) the active ingredient, (b) the composition and thickness of the enteric coating; (c) the composition and thickness of the seal coating; (d) the amount of active ingredient in individual beads; and (e) the size of the beads. Thus, the composition may be adjusted to allow release in the small intestine, the large intestine or throughout the intestinal tract. In addition, release rates can be controlled by applying an additional enteric coating over the gelatin capsule or over the Peltab after its formulation.

According to one embodiment of the present invention, the active core comprises an inert core, such as nonpareils provided in the form of sugar beads or sugar/starch beads, as well as the bisphosphonic acid or salt. Inert cores may be approximately 0.6 mm in diameter and are preferably from about 0.2 mm to about 1.0 mm in diameter. The bisphosphonic acid or salt thereof is loaded onto each of a plurality of the inert cores as an active coating. The bisphosphonic acid or salt may also be mixed with one or more additives before being loaded onto the inert cores. The additives may include, for example, a solubilizer and/or a lubricant. The bisphosphonic acid or salt (together with any additives) can be sprayed onto the inert core with a binder in a centrifugal coating apparatus. A polymer, such as HPMC, HPC or PVP may be applied in conjunction with the application of the active ingredient to form the active coating as a polymer film. A seal coating is applied around the active core, and the enteric coating is then provided around the seal coating on each of the active cores. This embodiment of the invention is particularly useful when the capsule form of the pharmaceutical composition is desired. A plurality of pellets containing the bisphosphonic acid or salt loaded on inert cores and coated with seal coatings and enteric coatings may be included in a capsule shell.

Another embodiment of the present invention is particularly useful if the Peltab form of the pharmaceutical composition is desired. In this embodiment, the active cores of the pellets comprise nonpareils provided in the form of sugar beads or sugar/starch beads onto which the bisphosphonic acid or salt has been loaded as described above. A seal coating is applied around the active core of each of the pellets, and the enteric coating provided around the seal coating on each of the active cores. A plurality of these pellets, which may be combined with one or more conventional additives, such as disintegrants and binders, may then be compressed into tablets generally known as Peltabs.

The following examples illustrate the invention. In each case, the active drug is a bisphosphonic acid or salt thereof, unless indicated otherwise. While sucrose (sugar) is the illustrated binding agent, other binding agents, such as polyvinylpyrrolidone, shellac or xanthan gum, may be used instead. Examples 1 through 3 present general examples of the preparation of pharmaceutical compositions containing bisphosphonic acids or salts thereof. Although, in principal, any bisphosphonic acid or salt may be used in the formulations, the formulations are particularly useful for preparing pharmaceutical compositions comprising alendronate sodium trihydrate.

EXAMPLE 1

Capsules:

A plurality of pellets containing the active drug are prepared from the following materials:

| Core: | |
| --- | --- |
| Nonpareil seeds | 95 mg |
| Active drug | 13.03 mg |
| Sucrose | 31.97 mg |
| Corn starch | 32 mg |
| Talcum | 10 mg |
| HPMC | 1 mg |
| | 183 mg |
| Water: as required | |
| Seal coating: | |
| HPMC | 7.2 mg |
| Talc | 1.4 mg |
| Propylene glycol | 1.4 mg |
| | 10 mg |
| Water: as required | |
| Isopropyl alcohol: as required | |
| Enteric coating: | |
| Eudragit L 100-55 | 22.50 mg |
| Sodium hydroxide | 0.320 mg |
| Triethyl citrate | 2.270 mg |
| Talc | 22.50 mg |
| Titanium dioxide | 2.18 mg |
| Aerosil | 0.23 mg |
| | 50.00 mg |
| Water: as required | |

The active drug, the sucrose, the corn starch and the talcum are blended thoroughly to yield a dusting powder. The nonpareil seeds are loaded into a centrifugal coater and then coated with the dusting powder while spraying the HPMC (hydroxypropyl methyl cellulose) solution. This procedure results in the production of a plurality of discrete pellets containing the active ingredient. The pellets so obtained are dried using conventional tray dryers or fluid bed dryers up to an outlet temperature of 45° C. These pellets are then seal coated using HPMC solution and further enteric coated in a suitable Wurster coater. The pellets are then included in a capsule shell.

EXAMPLE 2

Capsules:

A plurality of pellets containing the active drug are prepared from the following materials:

| Core: | |
|---|---:|
| Nonpareil seeds | 95 mg |
| Active drug | 13.03 mg |
| Sucrose | 31.97 mg |
| Corn starch | 32 mg |
| Talcum | 10 mg |
| HPMC | 1 mg |
| | 183 mg |

Water: as required

| Seal coating: | |
|---|---:|
| HPMC | 7.2 mg |
| Talc | 1.4 mg |
| Propylene glycol | 1.4 mg |
| | 10 mg |

Water: as required
Isopropyl alcohol: as required

| Enteric coating: | |
|---|---:|
| Eudragit L 100-55 | 18.00 mg |
| Sodium hydroxide | 0.25 mg |
| Triethyl citrate | 1.81 mg |
| Talc | 18.00 mg |
| Titanium dioxide | 1.75 mg |
| Aerosil | 0.19 mg |
| | 40.00 mg |

Water: as required.

The active drug, the sucrose, the corn starch and the talcum are blended thoroughly to yield a dusting powder. The nonpareil seeds are loaded into the centrifugal coater and then coated with the dusting powder while spraying the HPMC solution. This procedure results in the production of a plurality of discrete pellets containing the active ingredient. The pellets so obtained are dried using conventional tray dryers or fluid bed dryers up to an outlet temperature of 45° C. These pellets are then seal coated using HPMC solution and further enteric coated in a suitable Wurster coater. The pellets are then included in a capsule shell.

EXAMPLE 3

Peltabs:

A plurality of particles containing the active drug are prepared from the following materials:

| Core: | |
|---|---:|
| Nonpareil seeds | 110.07 mg |
| Active drug | 13.03 mg |
| Sucrose | 35.90 mg |
| Corn starch | 21.00 mg |
| Talcum | 2 mg |
| HPC-L Klucel | 1 mg |
| | 183 mg |

Water: as required

| Seal coating: | |
|---|---:|
| HPMC | 7.2 mg |
| Talc | 1.4 mg |
| Propylene glycol | 1.4 mg |
| | 10 mg |

Water: as required
Isopropyl alcohol: as required

-continued

| Enteric coating: | |
|---|---:|
| Eudragit L 100-55 | 22.50 mg |
| Sodium hydroxide | 0.320 mg |
| Triethyl citrate | 2.270 mg |
| Talc | 22.50 mg |
| Titanium dioxide | 2.18 mg |
| Aerosil | 0.23 mg |
| | 50.00 mg |

Water: as required

| | |
|---|---:|
| Microcrystalline cellulose | 50 mg |
| Croscarmellose sodium | 7 mg |
| | 57.00 mg |

The active drug, the sucrose, the corn starch and the talcum are blended thoroughly to yield a dusting powder. The nonpareil seeds are loaded into the centrifugal coater and then coated with the dusting powder while spraying the HPC-L Klucel (hydroxypropyl cellulose) solution. This procedure results in the production of a plurality of discrete pellets containing the active ingredient. The pellets so obtained are dried using conventional tray dryers or fluid bed dryers up to an outlet temperature of 45° C. The pellets are then seal coated using the HPMC solution and further enteric coated in a suitable Wurster coater. The pellets are then suitably diluted with binders and disintegrants and compressed by conventional means to form tablets.

The embodiments and non-limiting examples illustrated and discussed in this specification are intended only to teach those skilled in the art the best way known to the inventors to make and use the invention. Nothing in this specification should be considered as limiting the scope of the present invention.

The invention claimed is:

1. A pharmaceutical composition for the treatment of a disorder caused by the abnormal dissolution or deposition of calcium salts comprising:
    an inert core,
    an active coating surrounding the inert core,
    a seal coating surrounding the active coating,
    and an enteric coating around said seal coating;
wherein the active coating comprises at least one bisphosphonic acid or salt thereof.

2. The composition according to claim 1, wherein the at least one bisphosphonic acid is selected from the group consisting of:
    4-Amino-1-hydroxybutylidene-1,1-bisphosphonic acid;
    N-Methyl-4-amino-1-hydroxybutylidene-1,1-bisphosphonic acid;
    4-(N,N-Dimethylamino)-1-hydroxybutylidene-1,1-bisphosphonic acid;
    3-Amino-1-hydroxypropylidene-1,1-bisphosphonic acid;
    3-(N,N-Dimethylamino)-1-hydroxypropylidene-1,1-bisphosphonic acid;
    1-Hydroxy-3-(N-methyl-N-pentylamino)propylidene-1,1-bisphosphonic acid;
    4-(Hydroxymethylene-1,1-bisphosphonic acid)-piperidine; and
    salts thereof.

3. The composition according to claim 1, wherein the at least one bisphosphonic acid is alendronic acid.

4. The composition according to claim 1, wherein the at least one bisphosphonic acid or salt thereof is selected from the group consisting of alendronate sodium trihydrate, etidronate, clodronate, pamidronate, and ibandronate.

5. The composition according to claim 1, wherein the composition comprises from about 4% to about 40% by weight of the at least one bisphosphonic acid or salt thereof.

6. The composition according to claim 1, wherein the seal coating comprises one or more hydrophilic polymers selected from the group consisting of hydroxypropyl methylcellulose, hydroxypropyl cellulose, polyvinyl pyrrolidone, shellac, cellulose gum and xanthan gum.

7. The composition according to claim 1, wherein the enteric coating is selected from the group consisting of hydroxypropyl methylcellulose phthalate, hydroxypropyl cellulose acetyl succinate, cellulose acetate phthalate, polyvinyl acetate phthalate, methacrylic acid-methyl methacrylate copolymers, and mixtures thereof.

8. The composition according to claim 7, wherein the methacrylic acid-methyl methacrylate copolymer is an anionic polymer based on methacrylic acid esters.

9. The composition according to claim 1, wherein the inert core comprises sugar beads or sugar/starch beads.

10. The composition according to claim 1, wherein the active coating further comprises at least one of a solubilizer and a lubricant.

11. The composition according to claim 1, wherein the active coating comprises a polymer film comprising a mixture of at least one bisphosphonic acid or salt thereof and a polymer.

12. The composition according to claim 11, wherein the polymer is selected from the group consisting of hydroxypropyl methylcellulose, hydroxypropyl cellulose and polyvinyl pyrrolidone.

13. The composition according to claim 1, further comprising a binder.

14. A capsule or Peltab comprising a plurality of pellets each of which comprises a composition according to claim 1.

15. The composition according to claim 1, wherein the composition releases the at least one bisphosphonic acid or salt thereof only in the lower gastrointestinal tract of a human or animal upon ingestion.

16. The composition according to claim 1, wherein the disorder caused by the abnormal dissolution or deposition of calcium salts is selected from the group consisting of osteoporosis, osteodystrophy, Paget's disease, myositis ossificans, Bechterew's disease, cholelithiasis, nephrolithiasis, urinary calculus, arteriosclerosis, arthritis, bursitis, neuritis and tetany.

17. The capsule or Peltab of claim 14, further comprising an enteric coating over said capsule or Peltab.

18. A method for treating a disorder caused by the abnormal dissolution or deposition of calcium salts comprising:
providing a pharmaceutical composition; and
administering an effective dose of the pharmaceutical composition to a person in need thereof;
wherein the pharmaceutical composition comprises an inert core, an active coating surrounding the inert core, a seal coating surrounding the active coating, and an enteric coating around said seal coating; and wherein the active coating comprises at least one bisphosphonic acid or salt thereof.

19. The method according to claim 18 wherein the at least one bisphosphonic acid is selected from the group consisting of:
4-Amino-1-hydroxybutylidene-1,1-bisphosphonic acid;
N-Methyl-4-amino-1-hydroxybutylidene-1,1-bisphosphonic acid;
4-(N,N-Dimethylamino)-1-hydroxybutylidene-1,1-bisphosphonic acid;
3-Amino-1-hydroxypropylidene-1,1-bisphosphonic acid;
3-(N,N-Dimethylamino)-1-hydroxypropylidene-1,1-bisphosphonic acid;
1-Hydroxy-3-(N-methyl-N-pentylamino)propylidene-1,1-bisphosphonic acid;
4-(Hydroxymethylene-1,1-bisphosphonic acid)-piperidine; and
salts thereof.

20. The method according to claim 18, wherein the at least one bisphosphonic acid is alendronic acid.

21. The method according to claim 18, wherein the at least one bisphosphonic acid salt is selected from the group consisting of alendronate sodium trihydrate, etidronate, clodronate, pamidronate, and ibandronate.

22. The method according to claim 18, wherein the disorder caused by the abnormal dissolution or deposition of calcium salts is selected from the group consisting of osteoporosis, osteodystrophy, Paget's disease, myositis ossificans, Bechterew's disease, cholelithiasis, nephrolithiasis, urinary calculus, arteriosclerosis, arthritis, bursitis, neuritis and tetany.

* * * * *